United States Patent [19]

Branellec et al.

[11] Patent Number: 5,599,801
[45] Date of Patent: Feb. 4, 1997

[54] PURIFIED HEPARIN FRACTIONS, METHOD FOR OBTAINING THEM AND PHARMACEUTICAL COMPOSITIONS CONTAINING THEM

[75] Inventors: Jean-François Branellec, Mont Saint Aignan; José Espejo, Bois Guillaume; Philippe Picart, Rouen, all of France

[73] Assignee: Choay S.A., Paris, France

[21] Appl. No.: 239,320

[22] Filed: May 6, 1994

[30] Foreign Application Priority Data

May 7, 1993 [FR] France .................. 93 05534

[51] Int. Cl.$^6$ .......................... A61K 31/725; C08B 37/10
[52] U.S. Cl. .................. 514/56; 536/21; 536/124
[58] Field of Search ............... 514/56; 536/21, 536/124

[56] References Cited

U.S. PATENT DOCUMENTS

| | | | |
|---|---|---|---|
| 4,351,938 | 9/1982 | Barnett | 536/21 |
| 4,438,261 | 3/1984 | Barnett | 536/21 |
| 4,496,550 | 1/1985 | Lindahl et al. | 514/54 |
| 4,686,288 | 8/1987 | Lormeau et al. | 536/21 |
| 5,019,649 | 5/1991 | Lormeau et al. | 536/21 |
| 5,032,679 | 7/1991 | Brandley et al. | 536/21 |
| 5,366,900 | 11/1994 | Conboy et al. | 436/107 |
| 5,385,937 | 1/1995 | Stamler et al. | 514/557 |

FOREIGN PATENT DOCUMENTS

| | | |
|---|---|---|
| 0037319 | 10/1981 | European Pat. Off. . |
| WO82/03627 | 10/1982 | WIPO . |

OTHER PUBLICATIONS

Khan et al., *Polymer Photochemistry*, 6 (1985) 465–474.
Princz et al., *Wat. Supply*, 6 (1988) 199–205.

*Primary Examiner*—Gary L. Kunz
*Assistant Examiner*—Kathleen Kahler Fonda
*Attorney, Agent, or Firm*—Bacon & Thomas

[57] ABSTRACT

Heparin fractions obtained by nitrous depolymerization, containing at most 150 ppb of total N-nitroso compounds, prepared by subjecting heparins of natural origin which have been depolymerized with a nitrite to the action of UV radiation.

16 Claims, 2 Drawing Sheets

[5,599,801]

PURIFIED HEPARIN FRACTIONS, METHOD FOR OBTAINING THEM AND PHARMACEUTICAL COMPOSITIONS CONTAINING THEM

The present invention relates to purified heparin fractions, and more specifically to heparin fractions free from total nitroso compounds, to a method for preparing them and to medicinal products containing them.

More especially, the present invention relates to heparin fractions obtained by nitrous depolymerization which are practically devoid of nitroso compounds.

Heparin fractions are known to be obtained by nitrous depolymerization as described, for example, in Patent Applications EP-A-0,014,184 and EP-A-0,027,089. Some heparin fractions prepared by nitrous depolymerization are active principles of medicinal products which have come into common use under the name "low-molecular-weight heparins" or "heparins of small molecular mass". All details relating to low-molecular-weight heparins used as medicinal products, their assay and their degree of sulphation, expressed by the sulphate/carboxyl ratio, may be found by reference to the publication "Héparines de faible masse moléculaire" [Heparins of small molecular mass], Pharmeuropa, October 1991, 3, N. 3, pp. 161–165, as well as to the proposed monograph for the European Pharmacopoeia "Heparina massae molecularis minoris", February 1993 (PA/PH/Exp. 3T (92) 93). Some low-molecular-weight heparins thus prepared and which are useful as active principles of medicinal products are described in the patent applications or patents published under numbers FR-A-2478646, EP-A-0,037,319, EP-A-0,076,279 and EP-A-0,181,259. They are known under the International Non-proprietary Names (INN) nadroparin calcium, dalteparin sodium and reviparin sodium, and constitute active principles of specialities which are on the market or potentially so. In particular, reviparin sodium constitutes the active principle of the speciality CLIVARIN® marketed in Germany. Other low-molecular-weight heparins obtained by nitrous depolymerization are also present in some specialities at the disposal of the medical profession in Germany (MONO-EMBOLEX® NM), in Austria ( SANDOPARIN® and TROPARIN®) and in Switzerland (SANDOPARINE®) .

The method of nitrous depolymerization entails the formation of non-volatile nitroso compounds (hereinafter also referred to as N—NO compounds or quite simply N—NO) by addition of an —NO group to compounds susceptible to nitrosation present in heparin or in its fractions or fragments. Although the amount of nitroso compounds present in the heparin fractions is very small and is not detrimental to their use as medicinal products since the compounds in question are non-volatile, the manufacture of these products on an industrial scale entails the handling of large amounts of powders. It might hence be seen to be useful to remove them completely or almost completely in order to perfect the characteristics of the low-molecular-weight heparins which are used as active principles of pharmaceutical specialities.

In the case of low-molecular-weight heparins whose average molecular mass is small, for example in the case of a product which will be designated hereinafter CY 222 (average molecular mass from 1,700 Da to 3,300 Da), the amount of nitroso compounds may be higher than that of products having a higher molecular mass. This product fits the definition of the products claimed in the patent applications and patent published under numbers FR-2,478,646 and EP-0,037,319, and may be prepared according to the methods described in the same patent applications or patent.

It is hence highly desirable, for the reasons set out above, to be able to have available heparin fractions obtained by nitrous depolymerization and which are practically devoid of nitroso compounds.

A method for the removal of nitrates in drinking water with simultaneous sterilization of the water, by irradiation with ultraviolet rays at a wavelength below 200 nm, and preferably 185 nm, and at a basic pH, is described in the paper P. PRINCZ et al., Water Supply, 1988, 6, 199–205. Nevertheless, this document relating to water treatment did not enable it to be foreseen whether an irradiation with ultraviolet rays was applicable to a biologically active product without giving rise to adverse effects on its biological and/or physicochemical properties.

It has now been found that, by subjecting a heparin fraction obtained by nitrous depolymerization to the action of ultraviolet rays (hereinafter designated simply UV), the nitroso compounds present can be removed almost completely, and a purified heparin fraction having a content of total nitroso compounds equal to or even less than that of natural heparin is obtained.

It has also been found that, under the conditions used, UV radiation does not modify the structure of the heparin fractions, which retain all their biological and physicochemical properties.

Thus, according to one of its aspects, the present invention relates to heparin fractions obtained by nitrous depolymerization having a content of total nitroso compounds not exceeding 500 parts per billion (ppb), advantageously not exceeding 150 ppb, preferably not exceeding 100 ppb and still more preferably not exceeding 50 ppb, a content of 50 ppb being the minimum amount quantifiable in the present state of knowledge. The said fractions are preferably low-molecular-weight heparins.

According to an advantageous aspect, the invention relates to a purified low-molecular-weight heparin obtained by nitrous depolymerization, namely a depolymerized heparin obtained by nitrous depolymerization of heparin of natural origin preferably originating from porcine intestinal mucosa or from bovine lung or any other heparin extracted from tissues or organs of various animals, having the following characteristics:

an average molecular mass of less than 8,000 Da, at least 60% of all the constituents have a molecular mass of less than 8,000 Da, anti-factor Xa activity not less than 60 IU/mg, anti-factor Xa/anti-factor IIa activity ratio not less than 1.5, a content of total nitroso compounds not exceeding 500 ppb, advantageously not exceeding 150 ppb, preferably not exceeding 100 ppb and still more preferably not exceeding 50 ppb, the said depolymerized heparin being in the form of a pharmaceutically acceptable salt, preferably a sodium or calcium salt.

The anti-factor Xa activity and the anti-factor Xa/anti-factor IIa activity ratio are evaluated by reference to the international standard of low-molecular-weight heparins; reference WHO 1-85/600.

The above average molecular mass is determined according to the proposed monograph for the European Pharmacopoeia (see reference above).

In the present description the term "free from total nitroso compounds" is used to qualify the heparin fractions or low-molecular-weight heparins obtained by nitrous depolymerization and containing at most 500 ppb, advantageously at most 150 ppb, in particular at most 100 ppb and preferably at most 50 ppb of total nitroso compounds. The term "constituents" is used to denote the set of molecules of which low-molecular-weight heparin is composed.

The low-molecular-weight heparins free from total nitroso compounds which are the subject of the present invention have, in the majority of their constituents, a 2-O-sulpho-α-L-idopyranosuronic structure at the non-reducing end and a 6-O-sulpho-2,5-anhydro-D-mannitol structure at the reducing end, and a degree of sulphation which does not differ substantially from that of unfractionated heparin of natural origin. This degree of sulphation is between 2 and 2.5, and preferably between 2.0 and 2.3.

Advantageous low-molecular-weight heparins according to the present invention have variable molecular mass distributions, the molecular mass of 90% of their constituents ranging between 2,000 Da and 10,000 Da, preferably between 2,000 Da and 9,000 Da and advantageously between 2,000 Da and 8,000 Da. Moreover, these heparins have a preponderant molecular mass lying between 3,000 Da and 6,000 Da, and preferably between 4,000 Da and 5,000 Da.

Another preferred low-molecular-weight heparin according to the invention has a preponderant molecular mass ranging between 1,700 Da and 3,300 Da, the molecular mass of 90% of all the constituents ranging between 1,000 Da and 8,000 Da.

The term "preponderant molecular mass" is used to denote the molecular mass of the constituents of the heparin which correspond to the peak of the chromatographic profile obtained by exclusion chromatography, using a UV detector at $\lambda=205$ nm.

Purified CY 222, defined as the sodium salt of a depolymerized heparin obtained by nitrous acid depolymerization of heparin of natural origin from porcine intestinal mucosa, having:

a preponderant molecular mass ranging between 1,700 Da and 3,300 Da, 90% of the constituents having a molecular mass ranging between 1,000 Da and 8,000 Da, a 2-O-sulpho-α-L-idopyranosuronic structure at the non-reducing end and a 6-O-sulpho-2,5-anhydro-D-mannitol structure at the reducing end of the majority of its constituents, a degree of sulphation of approximately 2.1, an anti-factor Xa activity of 60–80 IU/mg, an anti-factor IIa activity not greater than 25 IU/mg, and more specifically of 10–15 IU/mg, a content of total nitroso compounds not exceeding 100 ppb ($1\times10^{-7}$ mg of nitroso compounds per mg of product), and preferably not exceeding 50 ppb ($5\times10^{-8}$ mg of nitroso compounds per mg of product), represents a preferred heparin fraction according to the present invention.

The heparin fractions free from total nitroso compounds (low-molecular-weight heparins) of the present invention are prepared according to another aspect of the present invention.

Thus, the present invention also relates to a method for the preparation of heparin fractions containing at most 500 ppb of total nitroso compounds, characterized in that an aqueous solution of a heparin fraction obtained by nitrous depolymerization is subjected to ultraviolet radiation.

As starting material, any heparin fraction obtained by nitrous depolymerization may be used. Such a starting material generally contains a content of total nitroso compounds lying between 1,000 and 20,000 ppb.

The determination of the total nitroso compounds is performed by the method of B. Pignatelli et al., described in Analyst, September 1989, 114, pp. 1103–1108 and in Analyst, July 1987, 112, pp. 945–949, adapted to heparin and its fractions, preferably to low-molecular-weight heparins.

The method of the present invention may be performed on a pharmaceutical grade low-molecular-weight heparin dissolved in water, or alternatively during the industrial manufacture, after the nitrous depolymerization step and before isolation of the pure pharmaceutical grade product. It is preferable to use a pharmaceutical grade low-molecular-weight heparin.

Thus, as starting material for the method of the present invention, any low-molecular-weight heparin obtained by nitrous depolymerization may be used. In order to obtain the maximum efficacy of the method, it is advantageous to use depolymerized heparin solutions free from suspended microparticles. The presence of these microparticles may be due to a poor dissolution of the depolymerized heparin or to various impurities, or alternatively to residues of reagents used in the depolymerization or in the purification. Various solutions of depolymerized heparin are hence preferably subjected to a prior filtration.

The method of the present invention is exceptionally effective and flexible, since it enables nitroso compounds to be removed simply, quickly and safely. In addition, the method of the invention does not give rise to any modification in the structure of the heparin fraction, the biological properties and physicochemical characteristics of which remain strictly identical.

The method of the present invention may be carried out by exposing a 5–15% m/V aqueous solution of heparin fraction obtained by nitrous depolymerization, preferably of low-molecular-weight heparin to be purified, under a UV radiation system at a wavelength of 180 to 350 nm, and preferably at 254 nm, at a temperature of 5° C. to 50° C., advantageously 15° C. to 35° C. and preferably at room temperature.

The pH of the solution is slightly acidic or slightly basic, in particular between 3 and 8, and preferably between 5 and 8.

The radiation time depends on the radiation system used, the power of the radiation and the amount of total nitroso compounds to be removed which are present in the heparin fraction. It is approximately 2 to 30 minutes, although purification is, in general, virtually complete after 9–15 minutes.

As a UV radiation system, it is possible to envisage either a static system or a dynamic system enabling solutions of heparin fractions to circulate around the UV radiation source. Dynamic systems are preferred. In this latter case, the UV radiation source may be combined with a cylindrical tube ("closed" type apparatus) or with a duct ("open" type apparatus). As a "closed" type apparatus, it is possible to use a JR1-50 (KATADYN) UV sterilizer or any other equivalent apparatus.

BRIEF DESCRIPTION OF THE DRAWINGS

FIG. 1 shows in section a "closed" type apparatus. This apparatus is composed of a UV lamp (1) around which a quartz sheath (2) is fitted. The solutions containing the low-molecular-weight heparins circulate around the UV lamp protected by the quartz sheath (sheath of circulating liquid (3)). They are introduced via an inlet (4) located at one of the ends of the UV lamp, the outlet (5) being located at the other end of the UV lamp.

Figure 1:
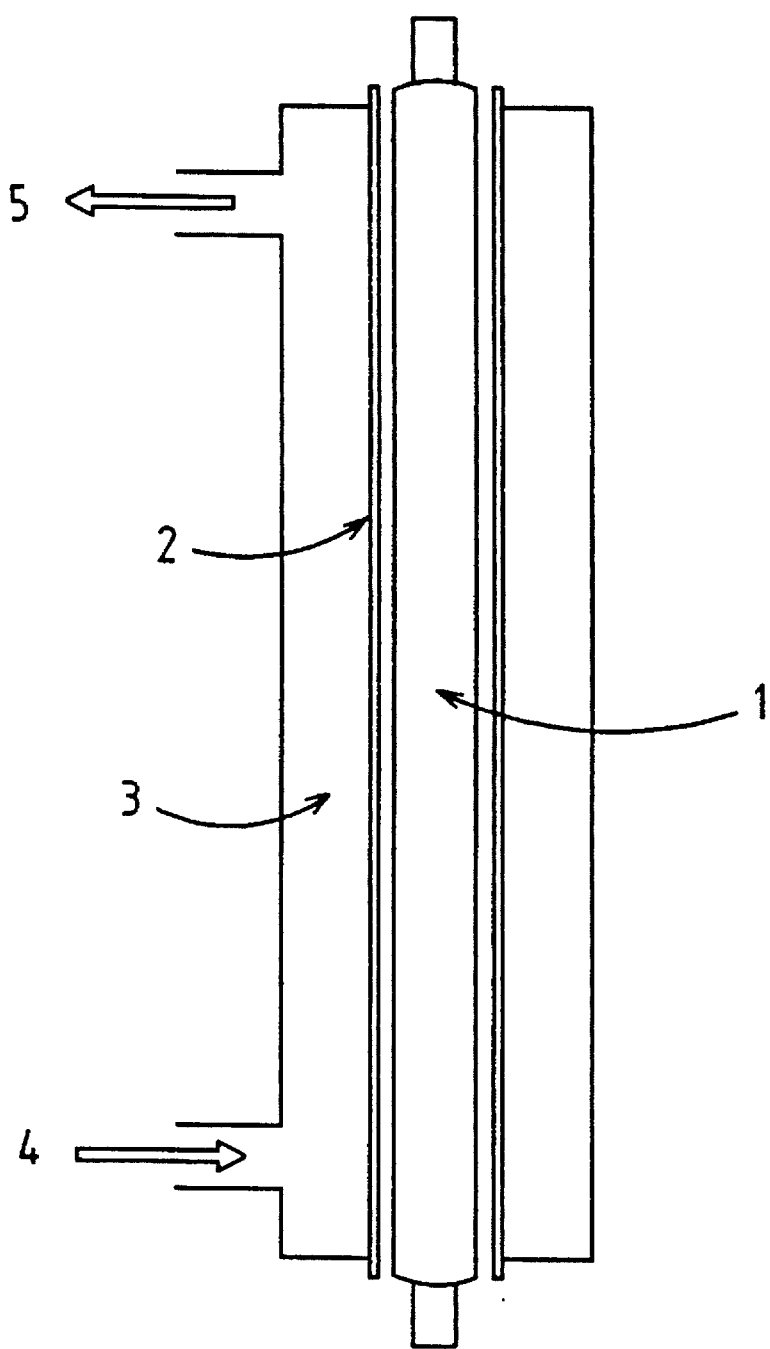
FIG. 1 is a schematic view of a closed type UV lamp used in an apparatus of the invention.

When a dynamic system is used, the flow rate of the solutions of the heparin fraction at which they circulate around the UV radiation source must be suitably adjusted in order to obtain the radiation time needed for removing the nitroso compounds. The different parameters which may be involved are the diameter of the stream of circulating liquid, the size and/or power of the UV radiation source, the heparin fraction concentration of the aqueous solution and the amount of nitroso compounds to be removed which is contained in this fraction.

The heparin fraction, or preferably low-molecular-weight heparin, free from total nitroso compounds thereby obtained may be recovered using conventional methods.

When a low-molecular-weight heparin which is already of pharmaceutical grade is used as starting material, it suffices to dissolve the product in water, to adjust the pH of the solution between 3 and 8, preferably between 5 and 8, and to subject this solution to the method of the present invention.

It is also possible to use as starting material unfractionated heparin of natural origin, advantageously in salt form, in particular heparin sodium, preferably originating from porcine intestinal mucosa. In this case, the method of the present invention constitutes one step in the preparation of the purified final product free from total nitroso compounds, after nitrous depolymerization. The overall method starting from heparin represents a further subject of the present invention.

Thus, according to another of its aspects, the present invention relates to a method for the preparation, by nitrous depolymerization, of a low-molecular-weight heparin having a content of total nitroso compounds not exceeding 500 ppb, advantageously not exceeding 150 ppb, preferably not exceeding 100 ppb and still more preferably not exceeding 50 ppb, characterized in that:

(a) a 5–15% m/V solution of unfractionated heparin sodium in water is treated with a solution of an alkali metal nitrite, preferably sodium nitrite, in the proportion of 15 to 69 g of nitrite per kg of heparin introduced, in the presence of hydrochloric acid at a pH of 1 to 5, and preferably 1.5 to 4, for a period of 20 to 50 minutes, and the product thereby obtained is subjected to a reduction, preferably in an alkaline medium, with 5–20 g of sodium borohydride per kg of heparin starting material, the excess sodium borohydride is destroyed with hydrochloric acid, the reaction medium is neutralized where appropriate and the product is precipitated with ethanol, then, after the low-molecular-weight heparin thereby obtained has been subjected, where appropriate, to one or more alcohol fractionations, (b) the solution thereby obtained is subjected to ultraviolet radiation, (c) a chromatographic purification is performed where appropriate and the depolymerized heparin sodium, purified and free from total nitroso compounds, is isolated by precipitation with sodium chloride and ethanol and, where appropriate, (d) the sodium salt is converted to another pharmaceutically acceptable salt, preferably the calcium salt.

According to a preferred aspect, the present invention relates to a method for the preparation of purified CY 222, defined as sodium salt of a depolymerized heparin obtained by nitrous acid depolymerization of heparin of natural origin from porcine intestinal mucosa, having:

a preponderant molecular mass ranging between 1,700 Da and 3,300 Da,

90% of the constituents having a molecular mass ranging between 1,000 Da and 8,000 Da, a 2-O-sulpho-α-L-idopyranosuronic structure at the non-reducing end and a 6-O-sulpho-2,5-anhydro-D-mannitol structure at the reducing end of the majority of its constituents, a degree of sulphation of approximately 2.1, an anti-factor Xa activity of 60–80 IU/mg, an anti-factor IIa activity not greater than 25 IU/mg, a content of nitroso compounds not exceeding 100 ppb, and preferably not exceeding 50 ppb, the said method being characterized in that:

(a) an aqueous solution of unfractionated heparin sodium of natural origin is treated with hydrochloric acid and an amount of an alkali metal nitrite of 3.5 to 4% by weight relative to the heparin introduced, while the pH is kept acidic and the presence of nitrous ions is monitored until there is a negative reaction, the mixture is then alcalinized, the product is reduced with sodium borohydride and the depolymerized product is isolated in a neutral medium by precipitation with ethanol, then (b) an aqueous solution of the product thereby obtained is passed at a pH of approximately 7 under an ultraviolet radiation system at 254 nm, the solution thereby obtained is thereafter introduced at the top of an anion exchange column and, after the column is rinsed with water and at a pH of approximately 7, the final product is recovered by precipitation with sodium chloride and ethanol.

In step (a), sodium nitrite is used, in the proportions described above, as the alkali metal nitrite.

Preferably, in step (b) of the method, the ultraviolet radiation system is equipped with a 16W lamp, and the time of exposure to UV radiation at 254 nm is 9–15 minutes approximately. A dynamic UV radiation system is preferred, and in particular an apparatus of the "closed" type. Advantageously, the concentration of the solutions subjected to UV radiation is 8–12% m/V.

According to a further aspect, the present invention relates to pharmaceutical compositions containing as active principle a purified heparin fraction free from total nitroso compounds, preferably a purified low-molecular-weight heparin free from total nitroso compounds, as is described above.

For the compositions according to the present invention, the heparin fraction can take the form of a lyophilisate, or can be in solution for subcutaneous injection in a sterile, biologically acceptable solvent such as water or in a physiological solution, in ampoules, in vials, in prefilled syringes or in self-injection devices of the "pen" type. Each unit of pharmaceutical dosage compositions can contain from 50 to 50,000 IU anti-factor Xa.

The heparin fractions according to the invention can also be administered by intravenous injection, alone or mixed with other active principles. They can, in addition, be administered by intranasal or intrapulmonary nebulization.

A preferred pharmaceutical composition according to the present invention contains as active principle CY 222 free from total nitroso compounds, as is described above, in dosage units containing from 10 mg to 5,000 mg of CY 222 in the form of the sodium salt.

As stated above, the determination of total nitroso compounds is performed by the method of B. Pignatelli et al., described in Analyst, September 1989, 114, pp. 1103–1108 and in Analyst, July 1987, 112, pp. 945–949, adapted to heparin and to low-molecular-weight heparins.

Analytical Method

The products to be analysed are preferably in powder form, consequently, in the case of determination of the total nitroso compounds present in a solution, a lyophilization of the said solution is first performed and the lyophilized sample is analysed afterwards.

1—Reagents

The reagents used for 100 mg of heparin fraction are as follows:

Ethyl acetate treated with 20% m/V sulphamic acid (a solution of 200 g of sulphamic acid in 1,000 ml of ethyl acetate, stirred for 3 days and filtered through paper before use), 15% hydrobromic acid in acetic acid (small amber vials with polyethylene stopper, containing 5 ml of 30% hydrobromic acid, closed under argon and stored in the dark. At the time of use, 5 ml of pure acetic acid are added, and the mixture is shaken and stored in a small container in the dark. One vial is used per series of assays), 95% formamide treated with 5% m/V sulphamic acid (a solution of 1 g of sulphamic acid in 20 ml of formamide containing 5% of purified water).

2—Preparation of Standard Solutions and of the Sample To Be Analysed

Standard Solution of N-nitrosodi-n-propylamine (NDPA)

78.62 g of pure ethanol are injected through the septum into a Sigma ISOPAC bottle containing 1 g of N-nitrosodi-n-propylamine. The concentration is 10,000 ppm of NDPA (3379 ppm of N—NO). The solution is then diluted to $1/100$ with pure ethanol and distributed in 0.5 ml aliquots in small capped vials. The concentration is 100 ppm of NDPA. The vials are stored in the dark at +4° C.

* Low standard solution: at the time of use, a dilution is made to $1/100$ in ethanol, then to $1/17$ in the treated formamide. The concentration will be 0.0588 ppm of NDPA, or 19.9 ppb of N—NO.
* Mid-range standard solution: at the time of use, a dilution is made to $1/61$ in ethanol, then to $1/11$ in the treated formamide. The concentration will be 0.149 ppm of NDPA, or 50.4 ppb of N—NO.
* High standard solution: at the time of use, a dilution is made to $1/10$ in ethanol, then to $1/10$ in the treated formamide. The concentration will be 1 ppm of NDPA, or 338 ppb of N—NO.

Sample to Be Analysed

The samples of heparin fraction are dried for 12 hours at 60° C. under vacuum, using phosphorus pentoxide. 100 mg of heparin fraction are dissolved in 1 ml of treated formamide and the mixture is shaken for 30 minutes on a shaker.

3—Apparatus Used

Figure 2:
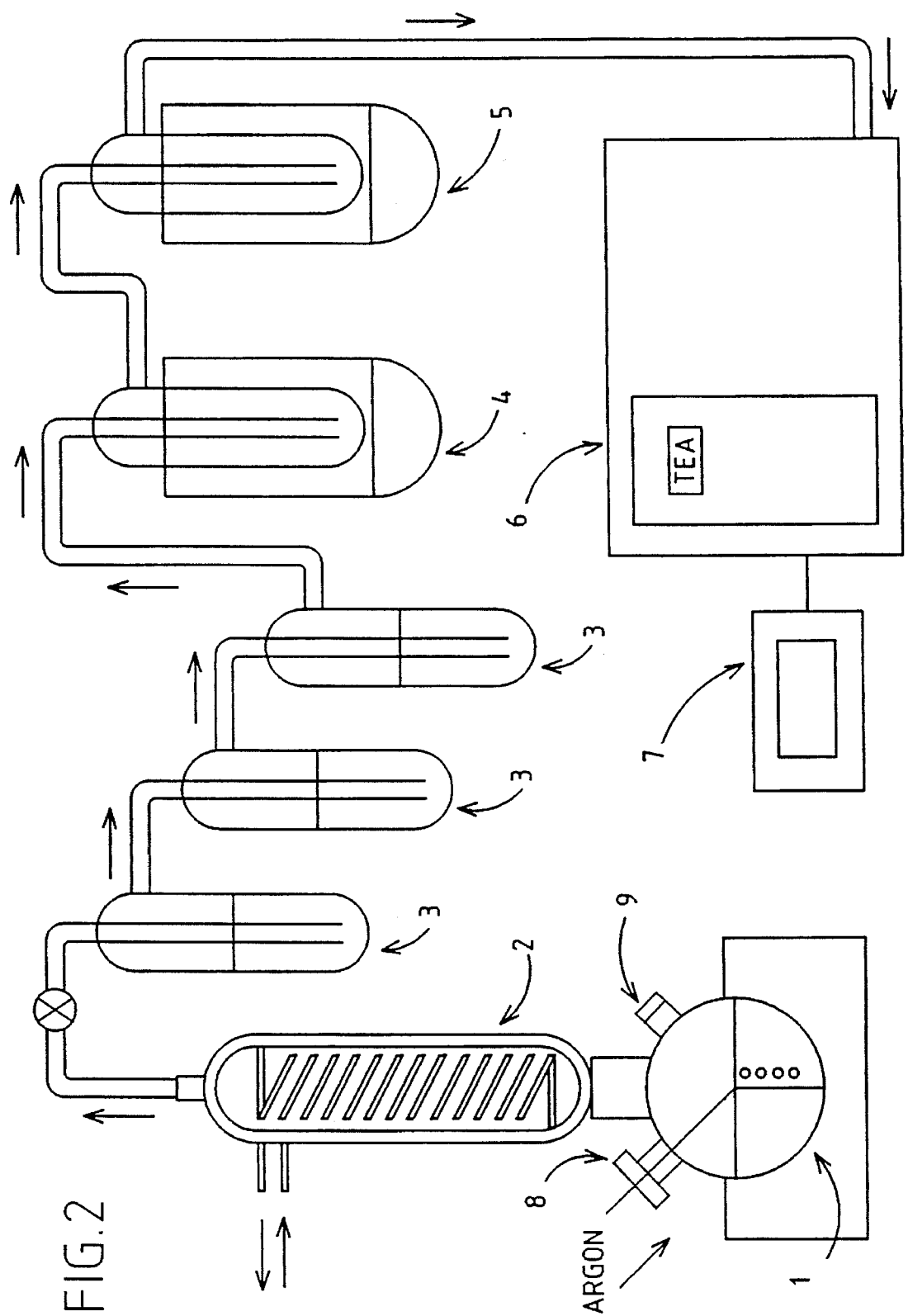
FIG. 2 shows an apparatus used in the purification method of the invention.

The apparatus used is illustrated in FIG. 2.

Assembly

The apparatus is composed of a 500 ml pyrex round-bottomed flask (1) surmounted by a double surface condenser (2) cooled to −15° C. The latter is connected to three bubblers mounted in series (3) each containing 30 ml of 30% sodium hydroxide. These bubblers are connected to two cold traps mounted in series, one prepared with molten ethanol at −120° C. (4) and the other with molten isopentane at −160° C. (5). These traps are lastly connected to a chemiluminescence detector (TEA) Model 610 (Thermedics Detection Inc.) or equivalent (6). The detector is connected to an integrator/recorder (7).

The flask is equipped on one side with a pierced stopper (8) enabling a cannula to be introduced through which a stream of argon is admitted. On the other side, a screw joint provided with a cap enables a GC type septum (9) to be attached, through which the sample is injected. The stream of argon and the vacuum produced by the vacuum pump of TEA draw the gases towards the TEA.

4—Operating Protocol

4.1—Setting the Detector

The TEA is set according to the manufacturer's instructions in order to obtain maximum sensitivity and reproducibility.

One hour before the assay, the oxygen supply is opened at a pressure of 2 bars and the flow rate is adjusted to 0.02 on the flow meter of the TEA 610 (Thermedics Detection Inc.).

4.2—Preparation of the Sodium Hydroxide Traps

Each trap is filled with 30 ml of 30% sodium hydroxide.

4.3—Preparation of the Cold Traps

−120° C. trap: Liquid nitrogen is poured gently while stirring with a wooden spatula into a Dewar containing 250 ml of ethanol until a paste is obtained. −160° C. trap: Liquid nitrogen is poured gently while stirring with a wooden spatula into a Dewar containing 250 ml of isopentane until a paste is obtained.

The two glass traps are placed in their respective Dewars and connected in series to the circuit.

4.4—Dehydration of the Flask-condenser Assembly 50 ml of ethyl acetate are refluxed for 1 hour under argon without connecting to the TEA.

4.5—Reaction and Assay 30 ml of treated ethyl acetate are introduced into a new clean and dry round-bottomed flask equipped with a septum, the flask is mounted under the condenser (the cryostat should be turned on 2 hours beforehand at −15° C.), the flask heater is placed in position and the flask is heated (position 4). The argon cannula is connected, the flow rate is adjusted to 0.1 l/minute and the freedom of the whole circuit from leaks is checked. Only the connection to the TEA remains open in order to avoid an excessive pressure. When the ethyl acetate is refluxing, a vacuum is applied very gently and at the same time the admission to the TEA is tightened up. A vacuum prevails throughout the circuit and reaches 2–4 mm of Hg when the system is equilibrated. Zero is set on the TEA at 10% full scale of the integrator/recorder.

Through the septum, there are injected successively 0.5 ml of purified water, 2 ml of dilute hydrobromic acid, then 2 ml of dilute hydrobromic acid again; between each injection, it is checked that the indicator returns to the baseline on the integrator/recorder. When the reagents have been injected into the flask, the indicator is allowed to return to the baseline and 50 µl of standard or of sample are then injected. Between injections, the indicator is allowed to return to the baseline. In the assays, 5 samples are sandwiched between 2 standards, and the procedure is carried out in such a way that the complete manipulation does not take more than 60 minutes.

4.6—Evaluation of the Amount of Total Nitroso Compounds

The amount of N—NO, in ppb, is calculated by the formula:

$$\text{ppb of N—NO} = \frac{\text{sample area} \times Cs \times 0.05 \times 44 \times 1000}{\text{standard area} \times 0.05 \times 0.1 \times 130.2}$$

where
Cs: concentration of the standard in ppm of NDPA (0.0588 or 0.149 or 1 ppm)
0.05: (numerator) test specimen of the standard (ml)
44: molecular mass of N—NO
1,000: conversion ppm to ppb
0.05: (denominator) test specimen of the sample (ml)
0.1: test specimen of sample in grams
130.2: molecular mass of NDPA.
The examples which follow illustrate the invention.

EXAMPLE 1

Preparation of Purified Nadroparin Calcium Having A Content of Total Nitroso Derivatives of Less Than 100 Ppb

Stage A: Depolymerization and Ethanol Fractionation

In a reactor, 20 kg of heparin sodium originating from porcine intestinal mucosa are dissolved with purified water so as to obtain a final concentration in the region of 10.3% (m/V). The pH of the solution is adjusted to 2.5 by means of concentrated hydrochloric acid.

572 g of sodium nitrite are introduced into the reactor while the pH is maintained at 2.5 by means of concentrated hydrochloric acid.

The depolymerization reaction is monitored using starch/potassium iodide test paper. Reaction is complete when the test is negative. The pH of the reaction solution is adjusted to 10 with concentrated sodium hydroxide, and 200 g of sodium borohydride are then added. The mixture is stirred for 15 hours, and the pH is then adjusted to between 4 and 3.5 using concentrated hydrochloric acid so as to destroy the excess borohydride. The pH is then adjusted to 7 by adding concentrated sodium hydroxide. The product is then precipitated by adding 2 volumes of ethanol per volume of aqueous solution. The precipitate is allowed to settle and the aqueous-alcoholic supernatant is then removed. The precipitate is dissolved in 400 l of purified water. Sodium chloride is added to this solution until a conductivity in the region of 20,000 µS/cm is obtained. The pH is then adjusted to a value in the region of 4 with concentrated hydrochloric acid, and 1 volume of absolute ethanol is added to the solution with stirring. The product is allowed to settle for approximately 60 hours and the aqueous-alcoholic supernatant is then removed. Nadroparin is thereby obtained in the form of the sodium salt.

The precipitate is then dissolved in purified water so as to obtain a solution at a concentration of approximately 18% m/V on the basis of the amount of heparin sodium introduced at the beginning, and the pH is adjusted to 7 using concentrated sodium hydroxide. The solution is then filtered on a system equipped with filter cartridges of porosity 0.2 µm. From the filtered solution containing nadroparin sodium, a sample is withdrawn which will not be treated according to the method described in Stage B (treatment by UV radiation). This sample is referred to as "control".

Stage B: Treatment by UV Radiation

For the treatment by UV radiation, a Katadyn type JR1-50 tube of useful volume 750 ml is used. The wavelength used is 254 nm. The running flow rate is appropriately adjusted (4,800 ml/hour) beforehand by means of a peristaltic pump using purified water, so as to obtain, with a run without recycling, a time of total exposure to UV of approximately 9 minutes. The solution of nadroparin sodium to be treated is then introduced, and the circuit is washed with purified water until the treated product has been recovered completely in the tank which is fitted to the outlet of the Katadyn JR1-50 tube.

Stage C: Purification by Chromatography and Conversion to the Calcium Salt

The nadroparin solution obtained in the preceding stage is purified on an anion exchange column (0.5 l/kg of heparin sodium introduced). The conductivity of the effluents collected is adjusted to 10,000–20,000 µS/cm with sodium chloride, and 1.5 volumes of ethanol are then added. The product is left to settle for approximately 41 hours and the supernatant is then removed.

The precipitate is dissolved in purified water (C=18% m/V on the basis of the amount of heparin sodium introduced), and calcium chloride hexahydrate (9.63 g/g of heparin sodium introduced) is added. An ethanol precipitation is then carried out by adding 1.5 volumes of ethanol. The salification step with calcium chloride hexahydrate and the purification step by ethanol precipitation are repeated. The precipitate obtained is dried at a temperature not exceeding 60° C.

Batch 1 is thereby obtained.

The "control" batch obtained in Stage A is also treated according to the method described in this Stage C, and the "control" batch of nadroparin calcium is isolated.

On a sample of Batch 1 and of the "control" batch of nadroparin calcium, physicochemical analyses are performed, as well as assays to determine their biological activity.

The various results are given in Tables I and II.

TABLE I

| | Physicochemical tests | |
|---|---|---|
| PARAMETER MONITORED | BATCH 1 (UV TREATMENT) | CONTROL (WITHOUT UV TREATMENT) |
| Total nitroso compounds | 53 ppb | 3,150 ppb |
| Free sulphates | 0.05% | 0.06% |
| pH of 5% solution | 6.0 | 6.0 |

TABLE I-continued

Physicochemical tests

| PARAMETER MONITORED | BATCH 1 (UV TREATMENT) | CONTROL (WITHOUT UV TREATMENT) |
|---|---|---|
| Free $NH_2$ HPLC-GPC (UV 205 nm) | <30 ppm | <30 ppm |
| Weight average molecular mass (Mw) | 5,017 Da | 4,933 Da |
| Number average molecular mass (Mn) | 4,043 Da | 4,052 Da |
| Peak molecular weight | 4,181 Da | 4,192 Da |
| Dispersion | 1.24 | 1.21 |
| % MW > 10,000 Da | 2.4 | 2.1 |
| % MW > 8,000 Da | 7.2 | 6.9 |
| % MW < 2,000 Da | 3.0 | 2.9 |
| % MW < 1,800 Da | 2.4 | 2.3 |

TABLE II

Biological tests

| PARAMETER MONITORED | BATCH 1 (UV TREATMENT) | CONTROL (WITHOUT UV TREATMENT) |
|---|---|---|
| Anti-factor Xa activity | 124 IU/mg | 123 IU/mg |
| Anti-factor IIa activity | 29.3 IU/mg | 30.4 IU/mg |

The results appearing in Tables I and II demonstrate that the UV treatment does not cause any degradation of nadroparin. In effect, the various physicochemical and biological characteristics of Batch 1, such as the chromatographic profile of the product, the content of the different impurities, the anti-factor Xa activity and the anti-factor IIa activity are identical to those of the control not treated by UV radiation, with a single exception. The content of total nitroso compounds in the untreated control is approximately 60 times as high as that of the total nitroso compounds in Batch 1 which has undergone a treatment by UV radiation.

Moreover, the results of electron paramagnetic resonance analysis confirmed that the treatment with UV radiation does not cause the release of free radicals.

EXAMPLE 2

Preparation of CY 222 Sodium Salt Having a Content of Total Nitroso Compounds of Less Than 50 Ppb Stage A: Depolymerization In a reactor, 250 g of heparin sodium originating for porcine intestinal mucosa are dissolved with purified water so as to obtain a final concentration in the region of 10.3% (m/V). The pH is adjusted to 2.5 by means of concentrated hydrochloric acid. 9.49 g of sodium nitrite are introduced into the reactor while the pH is maintained at 2.5. The depolymerization reaction is monitored using starch/potassium iodide test paper. Reaction is complete when the test is negative. The pH of the reaction solution is adjusted to between 10 and 10.5 with concentrated sodium hydroxide, and 2.5 g of sodium borohydride are then added. The mixture is left stirring for 15 hours, and the pH is then adjusted to between 3.5 and 4 using concentrated hydrochloric acid so as to destroy the excess borohydride. The pH is adjusted to 7 by adding concentrated sodium hydroxide. The product is then precipitated by adding 2 volumes of ethanol per volume of solution. The precipitate is allowed to settle and the supernatant is removed. CY 222 is thereby obtained in the form of the sodium salt. The product thereby obtained contains between 3,000 and 10,000 ppb of total nitroso compounds (results of 3 preparations).

Stage B: Treatment by UV Radiation

The precipitate of the preceding step is dissolved in purified water so as to obtain a final solution at a concentration of approximately 10% m/V on the basis of the amount of heparin sodium introduced, and the pH is adjusted to 7 with hydrochloric acid or sodium hydroxide. After the output of the pump has been adjusted, the solution thereby obtained is passed under an ultraviolet radiation system at 254 nm (Katadyn JR1-50 system provided with a 16W lamp). The time of exposure to UV radiation is 9 to 15 minutes.

Stage C: Purification by Chromatoqraphy and Final Precipitations

The solution obtained after treatment by UV radiation is purified on a chromatography column containing at least two liters of anion exchange resin per kg of heparin sodium introduced. The conductivity of the effluents collected is adjusted to 30–35 mS/cm using sodium chloride and their pH is adjusted to 7 using hydrochloric acid. 2 volumes of ethanol per volume of aqueous solution are then added. The precipitate is allowed to settle and the supernatant is removed. The precipitate is dissolved in purified water so as to obtain a final solution at a concentration of 20% m/V on the basis of the amount of heparin sodium introduced at the beginning, the conductivity of the solution is adjusted to 30–35 mS/cm with sodium chloride and the pH is adjusted to between 7 and 7.5 using concentrated hydrochloric acid or concentrated sodium hydroxide. The solution is then precipitated with 2 volumes of absolute ethanol and the precipitate is allowed to settle. The precipitate is collected, washed with ethanol and dried at a temperature not exceeding 60° C. Pure CY 222, defined as the sodium salt of a depolymerized heparin obtained by nitrous acid depolymerization of heparin from porcine intestinal mucosa, is thereby obtained, the product having:

a preponderant molecular mass ranging between 1,700 Da and 3,300 Da, 90% of the constituents ranging between 1,000 Da and 8,000 Da, a 2-O-sulpho-α-L-idopyranosuronic structure at the non-reducing end and a 6-O-sulpho-2,5-anhydro-D-mannitol structure at the reducing end of the majority of its constituents, a degree of sulphation of approximately 2.1, an anti-factor Xa activity of 60–80 IU/mg, an anti-factor IIa activity not greater than 25 IU/mg, and in particular of 10–15 IU/mg, a content of nitroso compounds of less than 50 ppb.

We claim:

1. A heparin fraction resulting from nitrous depolymerization of heparin of natural origin having a content of total N-nitroso compounds not exceeding 500 ppb.

2. The heparin fraction according to claim 1, which is a low-molecular-weight heparin.

3. The low-molecular-weight heparin according to claim 2, which is a depolymerized heparin resulting from nitrous depolymerization of heparin of natural origin, having the following characteristics:

an average molecular mass of less than 8,000 Da;

at bast 60% of all heparin constituents have an average molecular mass of less than 8,000 Da;

an anti-factor Xa activity not less than 60 IU/mg; and an anti-factor Xa/anti-factor IIa activity ratio not less than 1.5, in the form of a pharmaceutrically acceptable salt.

4. The low-molecular-weight heparin according to claim 3 in the form of a sodium salt or a calcium salt.

5. A sodium salt of depolymerized heparin resulting from nitrous acid depolymerization of heparin of natural origin, having:

a preponderant molecular mass ranging between 1,700 Da and 3,300 Da;

90% of heparin constituents having a molecular mass ranging between 1,000 Da and 8,000 Da;

a 2-O-sulpho-α-L-idopyranosuronic structure at the non-reducing end and a 6-O-sulpho-2,5-anhydro D mannitol structure at the reducing end of the majority of heparin constituents;

a degree of sulphation of approximately 2.1;

an anti-factor Xa activity of 60–80 IU/mg;

an anti-factor IIa activity not greater than 25 IU/mg; and a content of total N-nitroso compounds not exceeding 100 ppb.

6. The sodium salt of a depolymerized heparin according to claim 5, wherein the content of total N-nitroso compounds does not exceed 50 ppb.

7. A method of preparing a heparin fraction wherein an aqueous solution of a heparin fraction resulting from nitrous depolymerization is exposed to an effective amount of ultraviolet radiation to produce a heparin fraction according to claim 1.

8. The method according to claim 7, wherein an aqueous solution of a heparin fraction resulting from nitrous depolymerization, of concentration 5–15% m/V, is exposed to ultraviolet radiation at a wavelength of 180 to 350 nm, at a temperature of between 5° C. and 50° C. at a pH of the solution of between 3 and 8.

9. The method according to claim 7, wherein exposure takes place at 254 nm, at a temperature of between 15° C. and 35° C. and at a pH of between 5 and 8.

10. A method of preparing a low-molecular-weight heparin according to claim 1, comprising:

(a) treating a 5–15% m/V solution of a sodium salt of unfractionated heparin in water with a solution of sodium nitrite, in a proportion of 15 to 69 g of nitrite per kg of starting heparin, in the presence of hydrochloric acid at a pH of 1 to 5, for a period of 20 to 50 minutes; subjecting the product thereby obtained to a reduction, with 5–20 kg of sodium borohydride per kg of starting heparin; destroying the excess sodium borohydride with hydrochloric acid; neutralizing the reaction medium; precipitating the product with ethanol; and subjecting the low-molecular-weight heparin thereby obtained to one or more alcohol fractionations;

(b) subjecting the solution thereby obtained to ultra-violet radiation;

(c) performing a chromatographic purification, and isolating the depolymerized heparin sodium, purified and free from total N-nitroso compounds, by precipitation with sodium chloride and ethanol: and (d) isolating the sodium salt, and optionally converting the sodium salt to another pharmaceutically acceptable salt.

11. A method of preparing the salt according to claim 6, comprising:

(a) treating an aqueous solution of a sodium salt of unfractionated heparin with hydrochloric acid and an amount of an alkali metal nitrite of 3.5 to 4% by weight relative to the starting heparin, while the pH is kept acidic and the presence of nitrous ions is monitored until the presence of nitrous ions is no longer detected; rendering the mixture alkaline; reducing the product with sodium borohydride and isolating the depolymerized product in a neutral medium by precipitation with ethanol; and (b) exposing an aqueous solution of the product of step (a) at a pH of approximately 7 to ultraviolet radiation at 254 mn, introducing the solution thereby obtained at the top of an anion exchange column, and, after the column is rinsed with water at a pH of approximately 7, recovering the final product by precipitation with sodium chloride and ethanol.

12. The method according to claim 11, wherein, in step (b), the ultraviolet radiation at 254 nm is used for 9 to 15 minutes with a 16W UV lamp, and wherein the concentration of the solution of the product subjected to UV radiation is 8–12% m/V.

13. A pharmaceutical composition containing as active principle an effective amount of a heparin fraction as claimed in claim 11, together with a pharmaceutically acceptable carrier.

14. A pharmaceutical composition containing as active principle 10 mg to 5,000 mg of the salt of claim 6 per dosage unit, together with a pharmaceutically acceptable carrier.

15. The method of claim 10, wherein step (a) is carried out a pH 1.5 to 4.

16. The method of claim 10, wherein, in step (a), the reduction is carried out in an alkaline medium.

* * * * *